US008229194B2

(12) United States Patent
Grunkin et al.

(10) Patent No.: US 8,229,194 B2
(45) Date of Patent: Jul. 24, 2012

(54) FEATURE-BASED REGISTRATION OF SECTIONAL IMAGES

(75) Inventors: Michael Grunkin, Skodsborg (DK); Steen T. Rasmussen, Vaerlose (DK); Kim A. Bjerrum, Copenhagen NV (DK); Johan Dore Hansen, Naerum (DK)

(73) Assignee: Visiopharm A/S, Horsholm (DK)

( * ) Notice: Subject to any disclaimer, the term of this patent is extended or adjusted under 35 U.S.C. 154(b) by 525 days.

(21) Appl. No.: 12/514,918

(22) PCT Filed: Nov. 16, 2007

(86) PCT No.: PCT/DK2007/050171
§ 371 (c)(1),
(2), (4) Date: Jun. 3, 2009

(87) PCT Pub. No.: WO2008/080403
PCT Pub. Date: Oct. 7, 2008

(65) Prior Publication Data
US 2010/0215227 A1    Aug. 26, 2010

Related U.S. Application Data

(60) Provisional application No. 60/878,082, filed on Jan. 3, 2007.

(30) Foreign Application Priority Data
Nov. 16, 2006   (DK) .................................. 2006 01507

(51) Int. Cl.
*G06K 9/00* (2006.01)

(52) U.S. Cl. ........................................ 382/128; 382/133
(58) Field of Classification Search .................. 382/128, 382/133
See application file for complete search history.

(56) References Cited

U.S. PATENT DOCUMENTS

| 4,932,044 | A   * | 6/1990  | Williams et al. ................. 377/10 |
| 7,684,596 | B2  * | 3/2010  | Watson et al. .................. 382/128 |
| 2009/0304244 | A1 * | 12/2009 | Kolatt et al. ................... 382/128 |
| 2010/0142794 | A1 * | 6/2010  | Gardi et al. .................... 382/133 |

OTHER PUBLICATIONS

"Extending Unbiased Stereology of the Brain Ultrastructure to Three-Dimensional Volumes", John G. Fiala, Ph.D., Kristen M. Harris, Ph.D.; Journal of the American Medical Informatics Association, vol. 8, No. 1; Jan./Feb. 2001.

(Continued)

*Primary Examiner* — Joseph Chang
(74) *Attorney, Agent, or Firm* — Gifford, Krass, Sprinkle, Anderson & Citkowski, P.C.

(57) ABSTRACT

The present invention relates to a method and a system for obtaining and analysing image pairs, obtained as sections of specimen. The invention facilitates registration of two corresponding images, one from each section of the specimen. The invention includes performing a registration process of the two images thereby obtaining a mathematical transformation rule and afterwards using said transformation rule for each image field identified in one image allowing that the corresponding image field in the other image may be identified as well. After the corresponding image pairs have been obtained using the method of the present invention, the sections can be assessed, such as by identifying the counting events for at least one type of object on the image fields within at least one corresponding image pair, optionally using automatic means.

17 Claims, 13 Drawing Sheets

Adjacent sections are cut from the tissue, and corresponding positions in the two sections are examined to count events from first to second and from second to first section.

OTHER PUBLICATIONS

"Quantitative Histology Using Confocal Microsocpy: Implementation of Unbiased Stereology Procedures", Daniel A. Peterson; Methods 18, 493-507 (1999).

"A Standardized Method for Brain-Cutting Suitable for Both Stereology and MRI-Brain Co-Registration", C. Zarow, T.S. Kim, M. Singh, H.C. Chui; Journal of Neuroscience Methods; 139 (300-11 209-215).

* cited by examiner

Figure 2: Adjacent sections are cut from the tissue, and corresponding positions in the two sections are examined to count events from first to second and from second to first section.

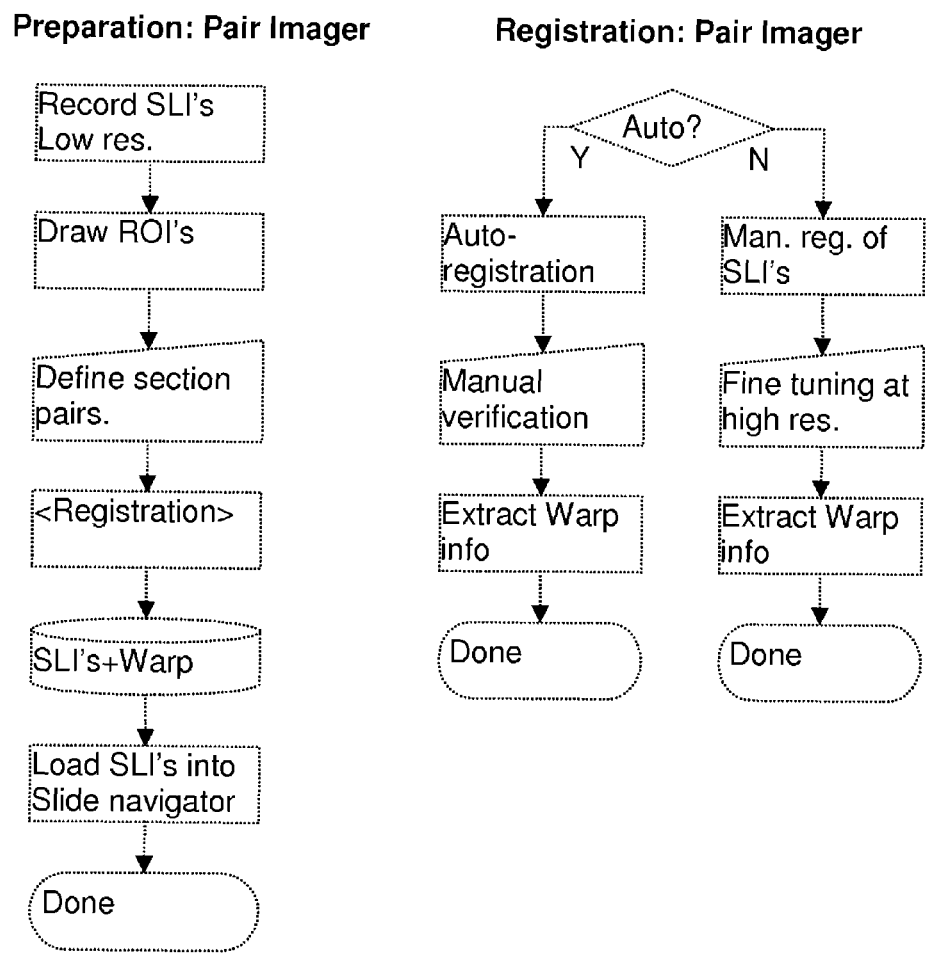
Fig 3: Examples of workflows for slide preparation and image registration

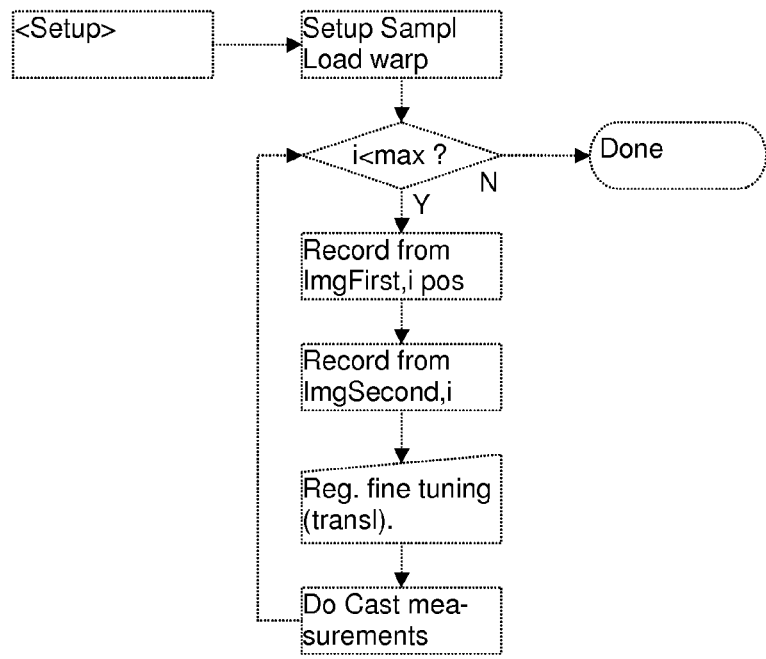
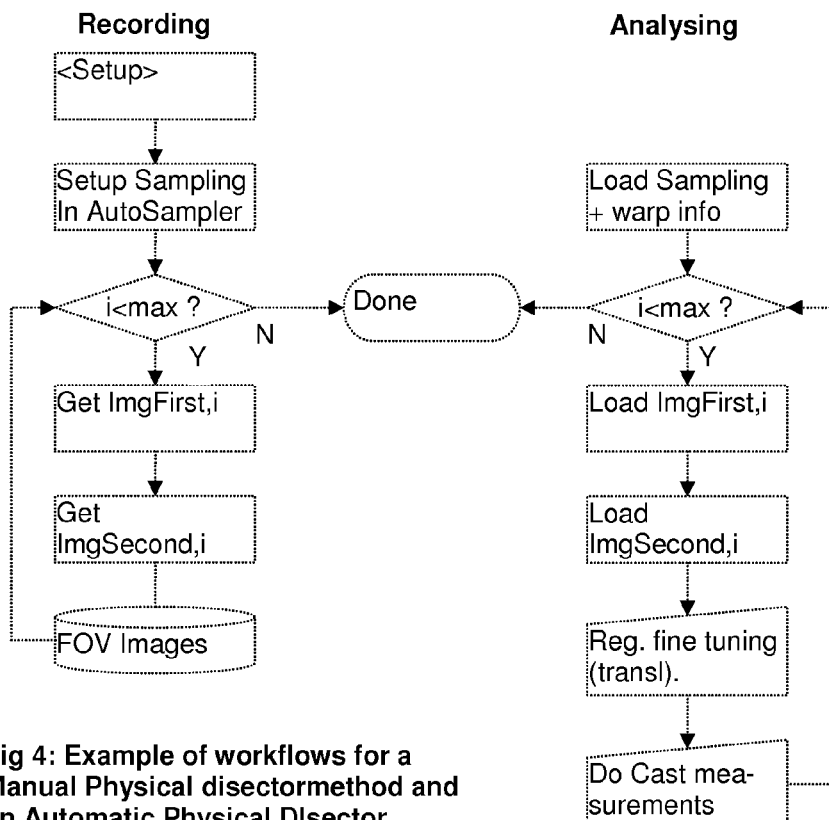
Fig 4: Example of workflows for a Manual Physical disectormethod and an Automatic Physical Disector Fig 5: Example of a workflow for creating sample pairs using an automatic physical disector
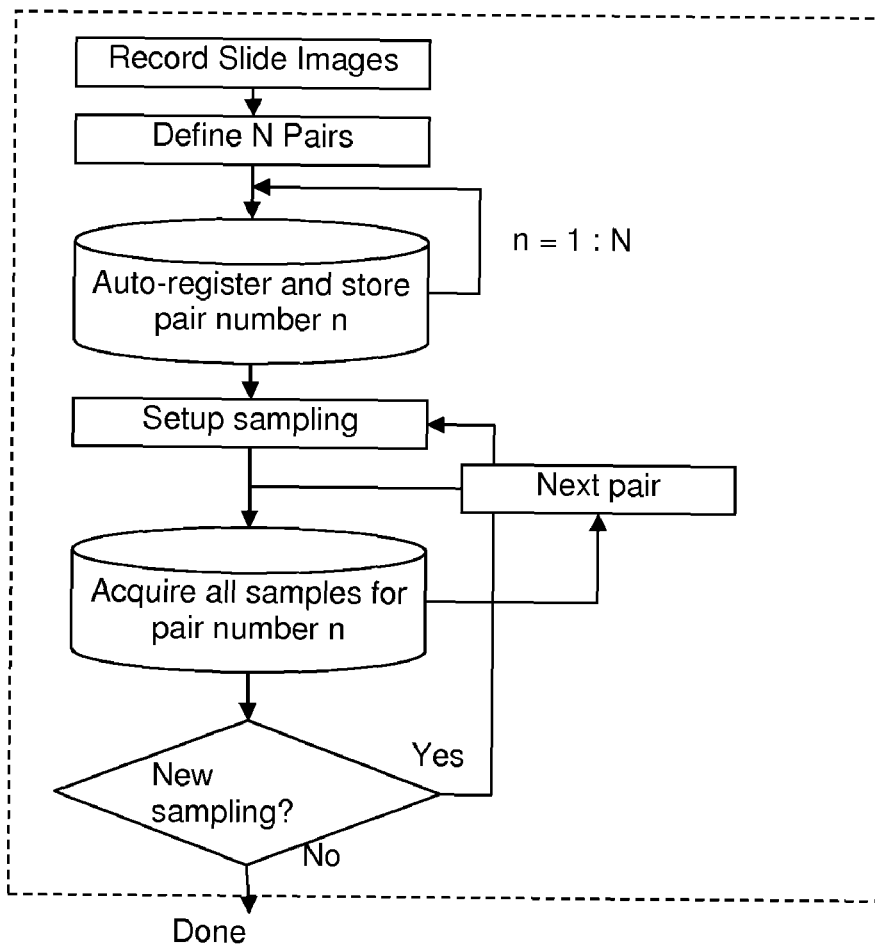

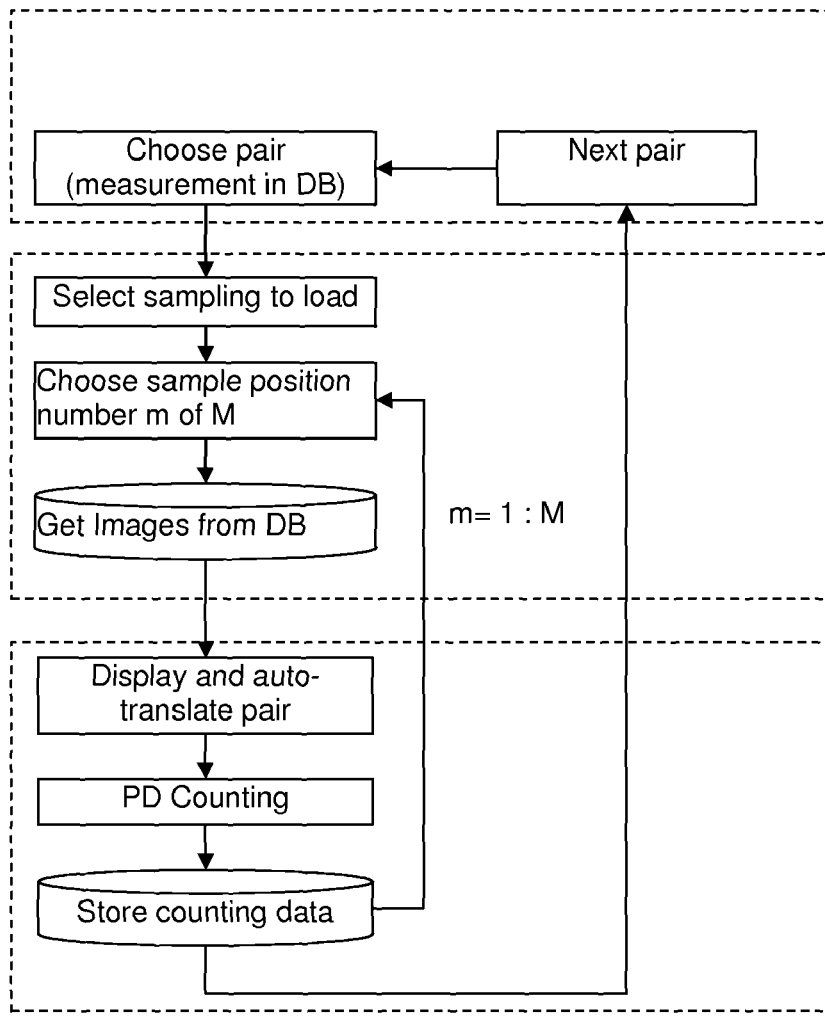
Fig 6: Example of a workflow for quantification of counting events using the Automatic Physical disector
PD= Physical disector

Fig 7: Example of a workflow for a Manual Physical disector
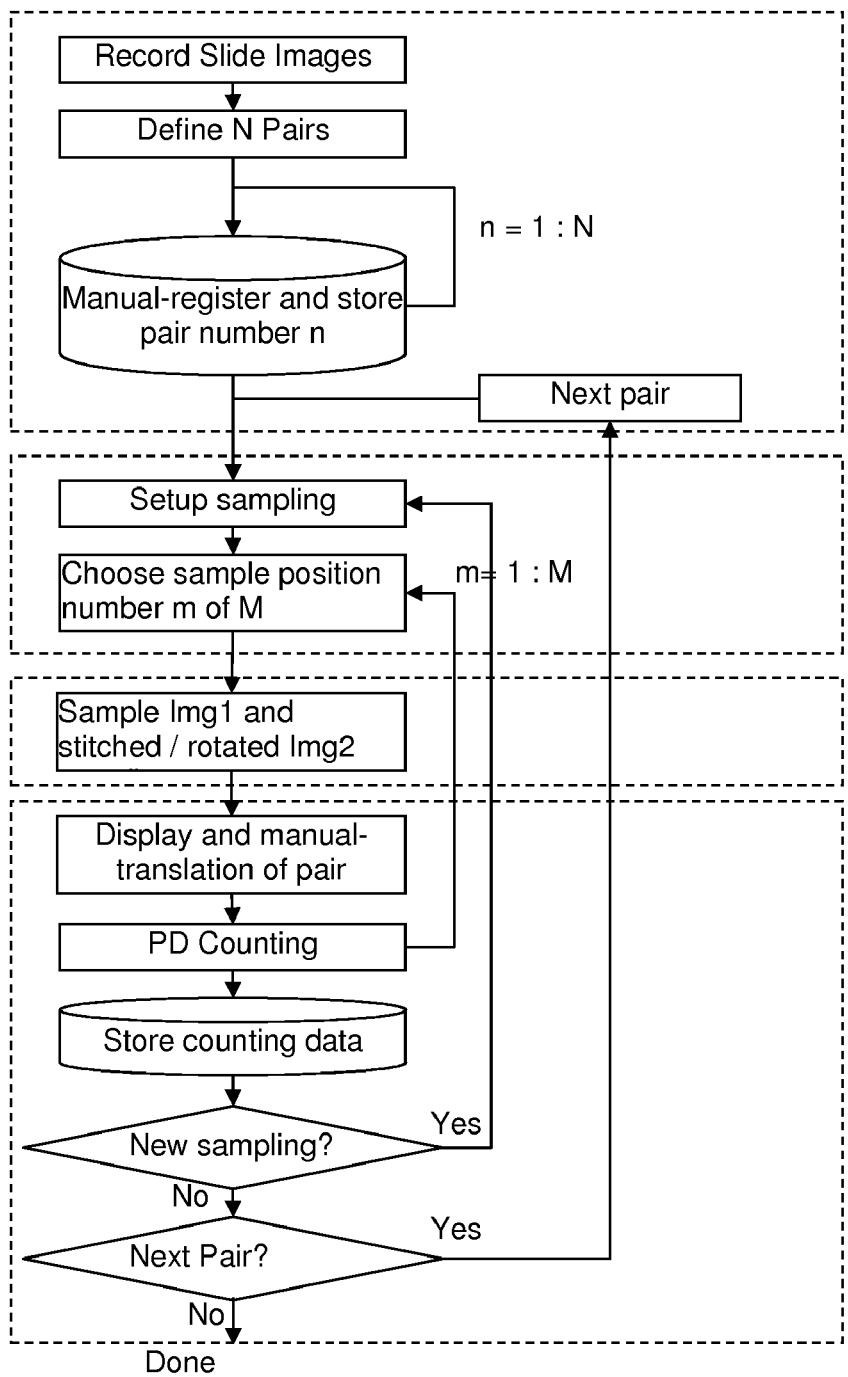

*Examples of Screen Dumps when using pairimager software*
*Figure 8a Super Image Acquisition*
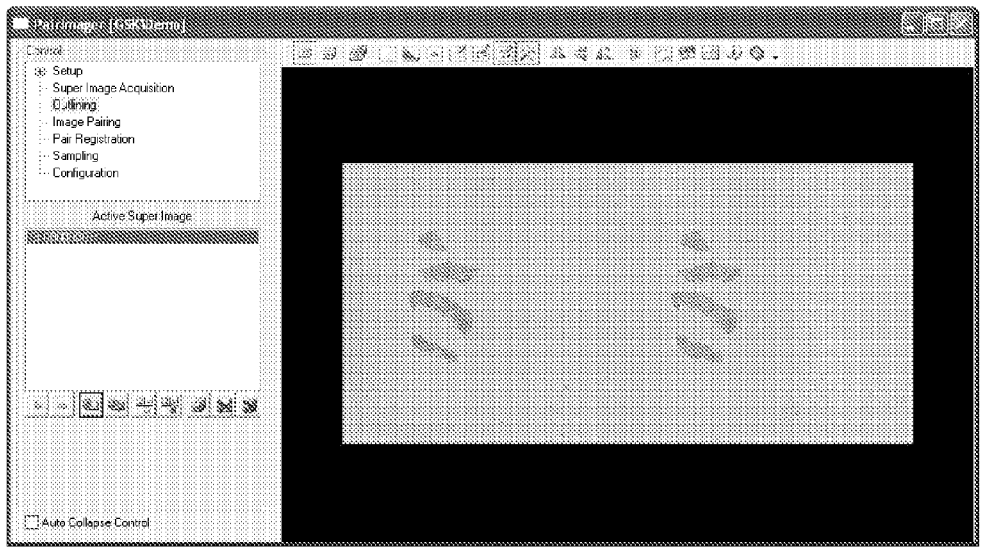
*Figure 8b Section detection*
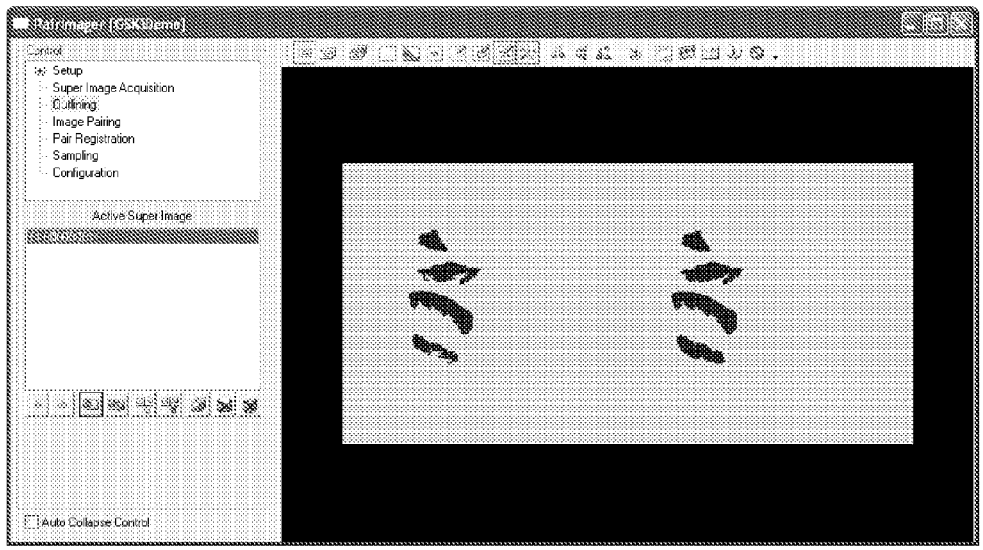

Figure 8c Section pairing
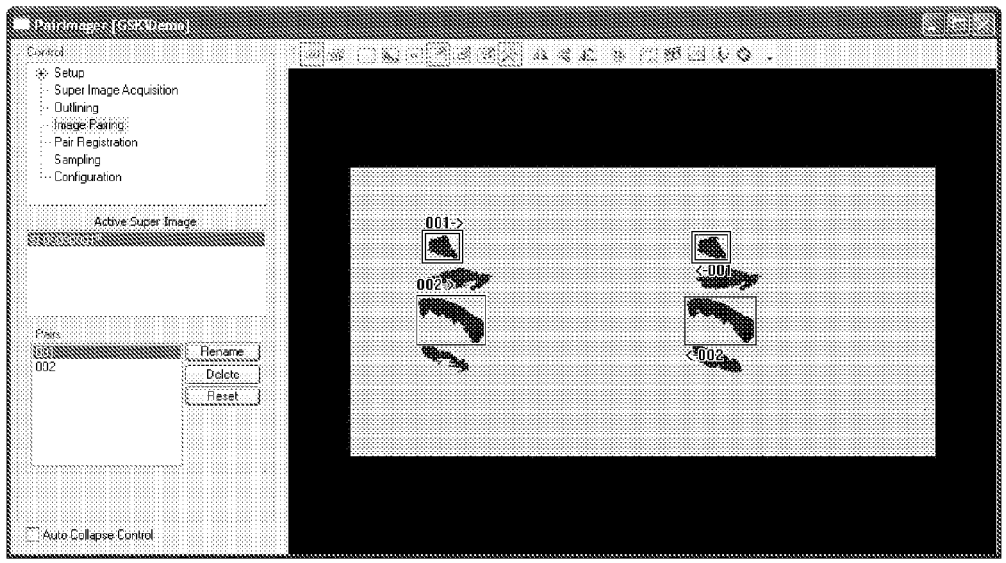
Figure 9a Section registration
Pair 1
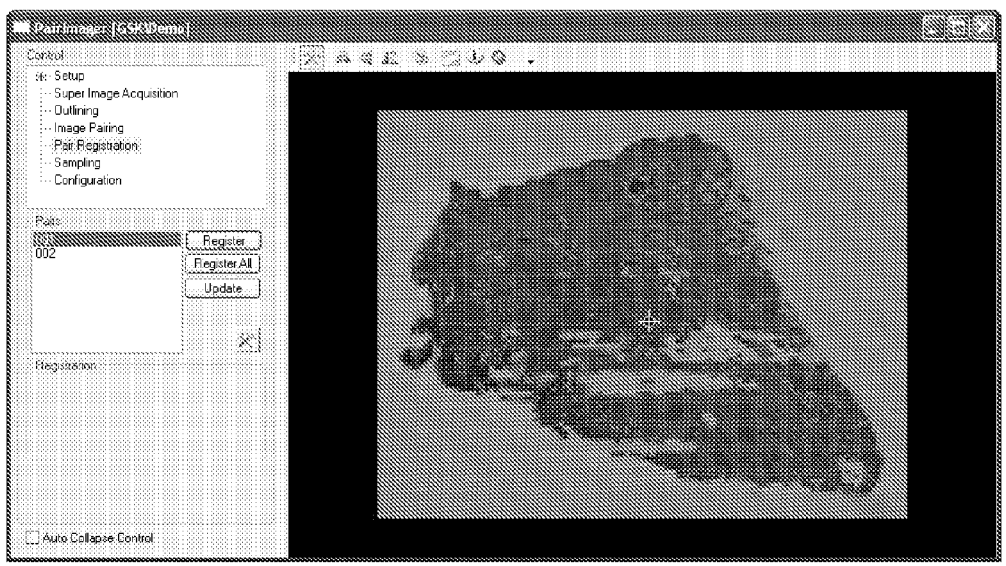
Pair 1, Section 1 before registration Pair 1, Section 2 before registration Pair 1, Section 1 and 2 overlay before registration

Figure 9d
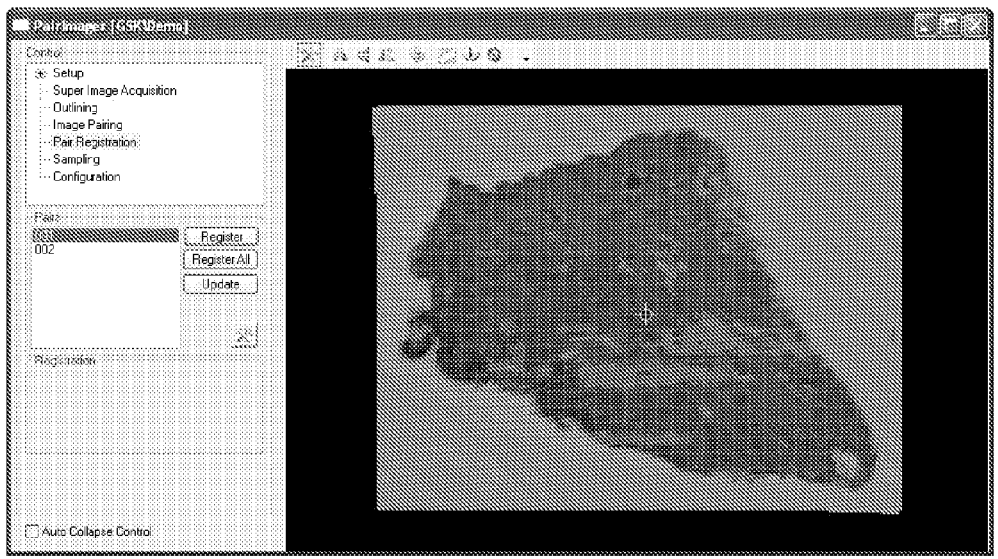
Pair 1, Section 1 and 2 overlay after registration
Figure 10a Pair 2
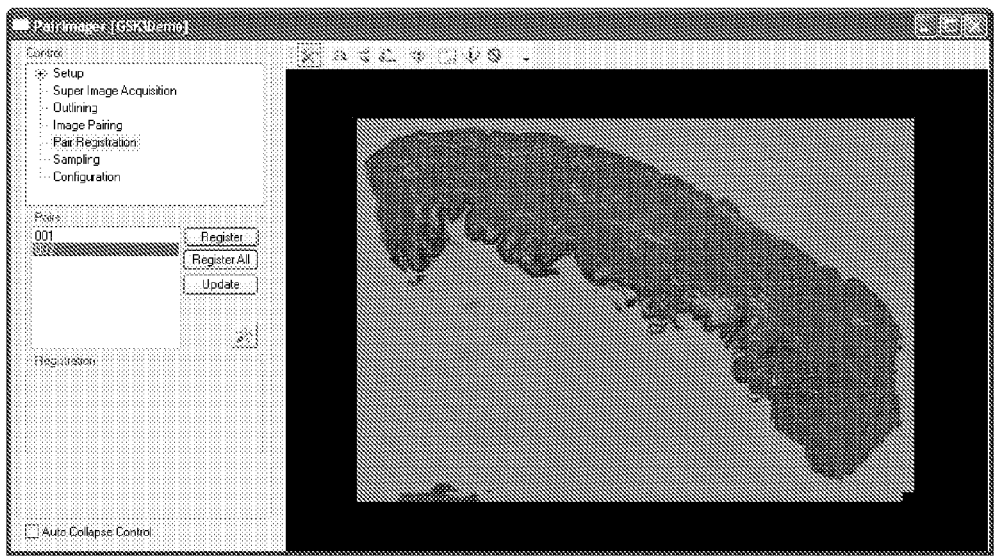
Pair 2, Section 1 before registration Pair 2, Section 2 before registration Pair 2, Section 1 and 2 overlay before registration Pair 21, Section 1 and 2 overlay after registration

FEATURE-BASED REGISTRATION OF SECTIONAL IMAGES

CROSS-REFERENCE TO RELATED APPLICATIONS

This application is the U.S. National Phase of PCT/DKC2007/050171 filed Nov. 16, 2007, which claims priority of U.S. Provisional Application 60/878,082 filed Jan. 3, 2007 and Danish Patent Application PA 2006 01507 filed Nov. 16, 2007.

All patent and non-patent references cited in the present application, are also hereby incorporated by reference in their entirety.

FIELD OF INVENTION

The present invention relates to methods for obtaining and analysing images, such as images obtained of a biological specimen.

BACKGROUND OF INVENTION

Quantitative Microscopy and Stereology

The ability to provide quantitative statements about microstructural tissue properties is becoming increasingly important in biopharmaceutical research and development in diverse applications related to both safety- and efficacy pharmacology.

Typically it is of interest to make quantitative statements about number, length, surface area, and volume of structural features reflecting the condition of an organ. It may even be of interest to investigate second-order properties based on the (number- or volume weighted) distribution of structural features.

There are real challenges and problems associated with the correct quantification of 3-D structural properties of tissues, of which some are related to expensive and labor intensive procedures, others to common misconceptions about the ability to infer 3-D information from 2-D histological sections.

Here, it is important to realize that objects (e.g. cells) in 3-D space that are cut by a 2-D section, as with a histological section, will be seen as profiles. Such 3-D objects will be hit by the 2-D section with a probability in proportion to their size, specifically their height normal to the section. Therefore, the objects of interest do not have the same probability of being counted, which is also the reason that e.g. counting of profiles is a significantly biased measure of the number of objects in 3-D space.

Therefore it is important to use methods that allow for making inference from 2-D sections to 3-D objects. This can be done using certain geometrical probes and estimators. The combination of sampling and the application of a set of unbiased geometrical probes in 3-D are collectively referred to as design-based stereology.

The stereological methods typically applied rely on simple counting of the number of times a feature is intersected by a suitable geometrical probe. To ensure that the intersections are zero-dimensional, i.e. a point that can be counted, the dimension of the probe and the feature under investigation must always sum to three:
  Points probe volume
  Lines probe surface
  Planes probe length
  Volumes probe number
(see FIG. 1)

The disector principle is very useful for estimating the number of discrete objects as e.g. cells within a well defined reference space. This principle is widely used, and is perhaps the one area in which design-based stereology has had its largest impact to date. The principle also represents some special challenges seen from an automation point of view.

The major breakthrough in assumption-free, unbiased (stereological) counting was provided by the publication of the Physical Disector paper [Howard & Reed]. The disector consists of a pair of serial sections a known distance apart. The method relies upon the principle that if a particles transect (profile) is seen in one section and not the next, it is counted (this is a counting event).

The physical disector principle is used in a number of frequently occurring situations, for example when the structures of interest are very large, if the tissue is not sufficiently transparent to allow for the use of an optical disector, or when the staining, whatever reason, cannot penetrate sufficiently deep into the tissue under investigation.

The physical disector uses, as the name suggests, at least two adjacent or serial physical sections from the tissue under investigation.

FIG. 2 illustrates two corresponding fields of view sampled from two registered sections of tissue. Using the upper image as reference and the lower image as look-up counting events are identified.

In practice, it is found that most of the time spent in applying a physical disector is dedicated to registering the two sections. Therefore, in order to increase the overall efficiently, counting is done both ways—i.e. by reversing reference and look-up.

Image registration of sections required for the physical disector method rely on spatial mapping and based on both structural/textural and intensity differences between two images. Many types of distortions can be present between images of the two sections to be registered. The task of registration is to select the transformation method, which will remove only the spatial distortions between the images due to difference in acquisition and not due to differences in scene characteristics. With the help of geometric transformations, the spatial relationships between pixels in the images can be modified. A geometric transformation consists of two basic operations: a spatial transformation and a gray-level interpolation. The spatial transformation defines the mapping of the new pixel locations in the output image according to the pixel locations in the input image. There are several methods that can be used for gray level interpolation. For example the nearest neighbor approach, cubic convolution interpolation and bilinear interpolation. For Gray level interpolation, the new pixel coordinates (x1, y1) are calculated by means of the spatial transformation. Digital images are used, therefore the original coordinates have integer values. Depending on the values of the parameters, the new coordinates, (x',y') can become noninteger values. Since the distorted image i2 is digital, its pixel values can only be defined at integer coordinates. Thus using noninteger values for x' and y' causes a mapping into locations of i2 for which no gray levels are defined. The gray level values of these noninteger points should be based on the integer point locations around the noninteger points.

An Unbiased counting frame comprising an area of an image field is preferably used in the process of enumeration counting events in a given disector pair. The unbiased counting frame has an acceptance boundary and a "forbidden" boundary, as shown in FIG. 11. Any particles intersecting the "forbidden" line may not be counted. Particles which are situated inside the counting frame or those that intersect with the acceptance line but not the "forbidden" line may be counted. In FIG. 1, the counting is carried out according to these simple rules.

In the context of the physical disector, counting events are included according to these rules. Thus a cell nucleus is only counted if it is a counting event and fall inside the counting frame as described above. It is only a counting event if it is found in the reference image, but not in the look-up image.

The total amount micro-structure in a volume, such as e.g. number of cells, is based on estimation principles. An estimator is a tool that, given data, is capable of providing an estimate. Typically, the estimators used in stereology provide estimates of the amount of a feature per unit reference volume. Typically the following ratio quantities, generally known as densities, are used:

Volume density: $V_V$ The volume proportion of one phase within a reference volume Surface density: $S_V$ The area of an interface within a unit reference volume Length density: $L_V$ The length of a linear feature within a unit of reference volume Numerical density: $N_V$ The number of discrete objects in a unit reference volume In biological systems, the definition of the reference space is crucial. The fundamental sampling unit (FSU) is related to the organism/organ of interest. It is only in the knowledge of the size of the reference space that the nature of any variation or lack thereof can be fully understood.

In many situations this can be accomplished using advanced image segmentation techniques, that allows for simple test of whether or not a geometrical probe intersects with a given (segmented) structure in field-of-view.

Stereology software is commercially available. The most widespread packages are probably the StereoInvestigator by MicroBrightfield and the CAST system by Visiopharm (taken over by Visiopharm A/S from Olympus Denmark A/S).

Even with careful planning and using the physical disector principle, the procedure of obtaining quantification based on design based stereology is still time consuming and labor intensive and certainly not ideally suited for screening purposes or even moderate-volume routine purposes.

Human operators are required for accessing the physical slide and mounting it on a stage under the microscope. Even with software controlling the systematic random sampling, it is necessary to wait while the stage is moving to the next sampling position. Significant time is used for focusing and other adjustments before counting can commence.

Thus, a major obstacle so far has been the inability to deal with microscope slides in the digital domain.

SUMMARY OF INVENTION

The present invention relates to a method and a system for obtaining and analysing image pairs, obtained as sections of specimen. The invention facilitates registration of two corresponding images, one from each section of the specimen.

In one aspect of the present invention is provided a method for obtaining at least one corresponding image pair from at least two adjacent sections A and B of a specimen. Said method comprises the steps of:— a) obtaining a superimage of at least part of section A and a superimage of at least part of section B, b) carrying out an image registration process on the two superimages by establishing correspondence between features of the two related superimages, in order to obtain a mathematical transformation rule, c) identifying an image field within section A, d) using said mathematical transformation rule to identify a corresponding area within section B, said area comprising an image field within section B corresponding to said image field within section A, e) acquiring an image of said image field within section A identified in step c) and acquiring an image of said image field within section B identified in step d) to obtain a corresponding image pair, f) optionally repeating steps c)-e) one or more times to obtain one or more different corresponding image pair(s) of one or more different image fields in the two sections A and B, g) storing a digitized version of said corresponding image pair(s) in a computer-readable storage means.

Optionally, the method can comprise the additional step of carrying out a second registration process on the two images obtained in step e) to obtain a registered corresponding image pair. Furthermore, step f) of the method can optionally be repeated to obtain at least two image pairs, such as at least three, for example at least four, such as at least five, for example at least six, such as at least seven, for example at least eight, such as at least nine, for example at least ten, such as at least 15, for example at least 20, such as at least 25, for example at least 50.

The specimen is preferably a biological sample, such as a tissue section.

After the corresponding image pairs have been obtained using the method of the present invention, the sections can be assessed, such as by identifying the counting events for at least one type of object on the image fields within at least one corresponding image pair, optionally using automatic means. The counting events are preferably quantified, such as by adding the number of counting events and/or objects per volume of tissue, such as obtaining an estimate of the number, such as the total number, of objects or structures in the reference volume together with other relevant statistics, including e.g. a confidence interval for the estimate.

In another aspect, the present invention relates to a computer readable medium comprising instructions for carrying out at least one of the methods according to the present invention.

In another aspect, the present invention relates to an automated system suitable for carrying out the method according to the present invention, preferably comprising, in combination:

a database capable of including (storing and retrieving) a plurality of digital images of a plurality of biological specimens;

a software module for analyzing a plurality of pixels from a digital image of a biological specimen;

a control module comprising instructions for carrying out the method.

The physical disector previously described requires perfect registration between two adjacent sections. This is currently one of the most time-consuming aspects of using the physical disector. The present invention provides many improvements over the prior art physical disectors, not least in the improved registration methods and the fact that counting can occur "offline".

DRAWINGS

FIG. 2 shows Adjacent sections are cut from the tissue, and corresponding positions in the two sections are examined to count events from first to second and from second to first section.

FIG. 3 shows examples of workflows for slide preparation and image registration.

FIG. 4 shows examples of workflow for manual and automatic physical disector.

FIG. 5 shows an example of a workflow for creating sample pairs using an automatic physical disector.

FIG. 6 shows an example of a workflow for quantification of counting events using the automatic physical disector.

FIG. 7 shows an example of a workflow for a manual physical disector.

FIG. 8 shows examples of screen dumps when using a pair imager software, wherein 8a is super image acquisition, 8b is section detection, and 8c is section pairing.

Figure 1:
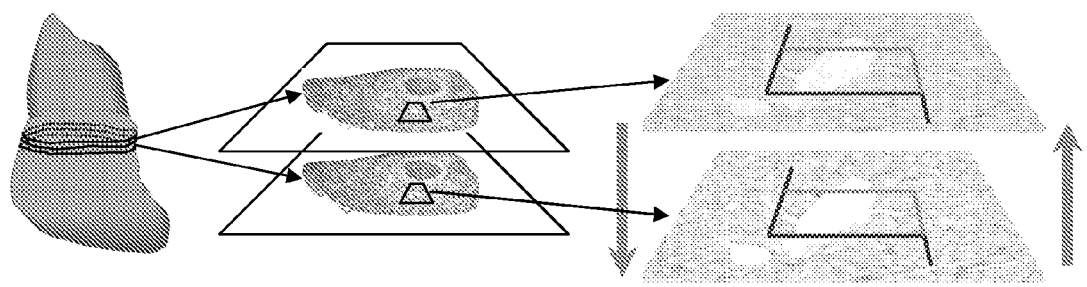
FIG. 1 shows that the sum of dimensions for probe and measured feature is always 3. E.g. with a line probe (1 dimension), it is possible to measure surface areas (2 dimensions).
Figure 9B:
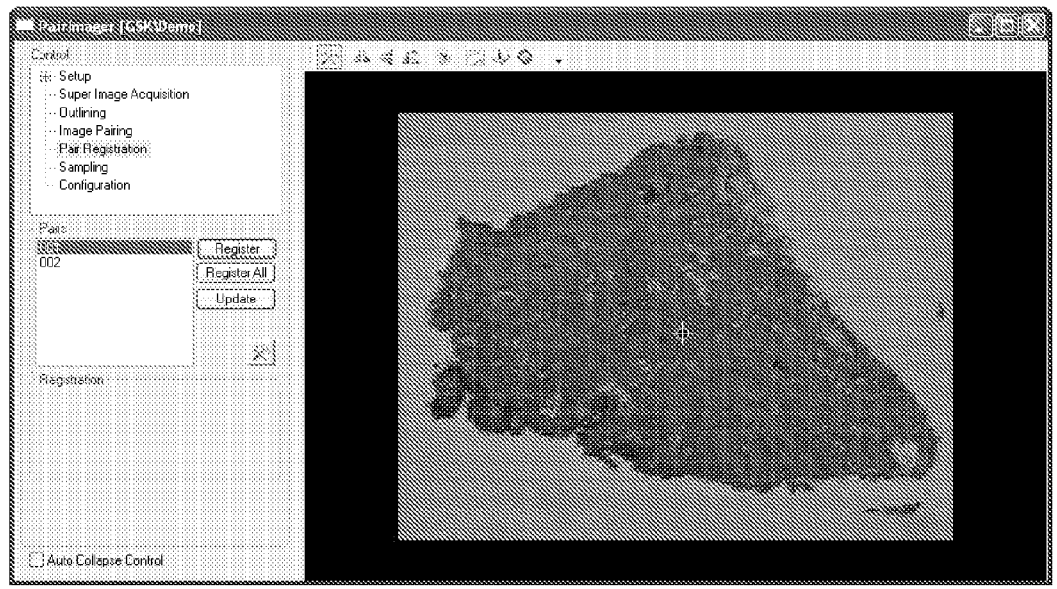
Figure 9C:
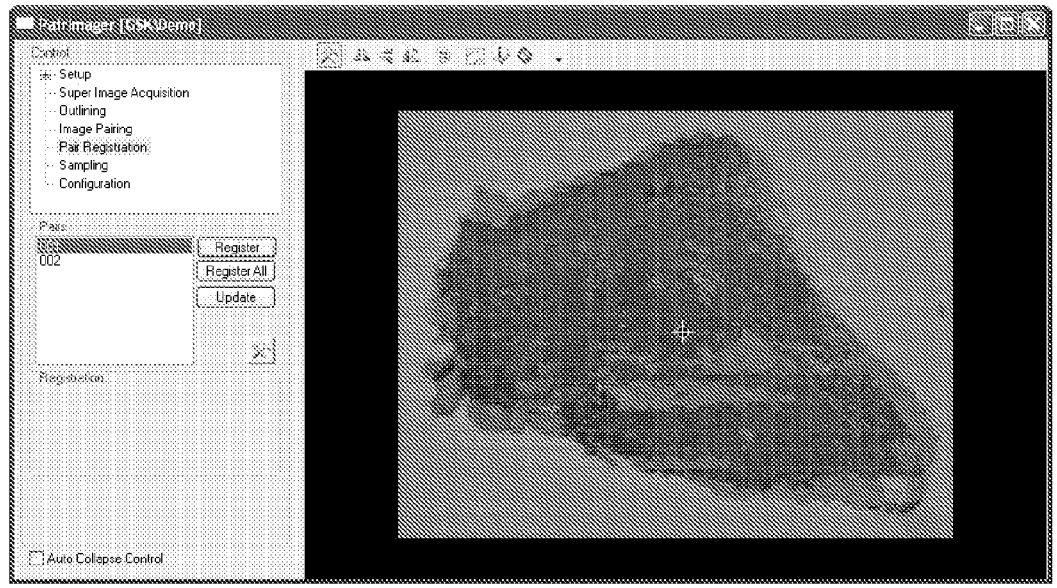

FIG. 9 shows screen dumps for section pairing and section registration of pair 1 in FIG. 8, wherein 9a shows before registration, and 9b overlay before registration, and 9c the two sections after registration, and 9d the overlay after registration.

Figure 10B:
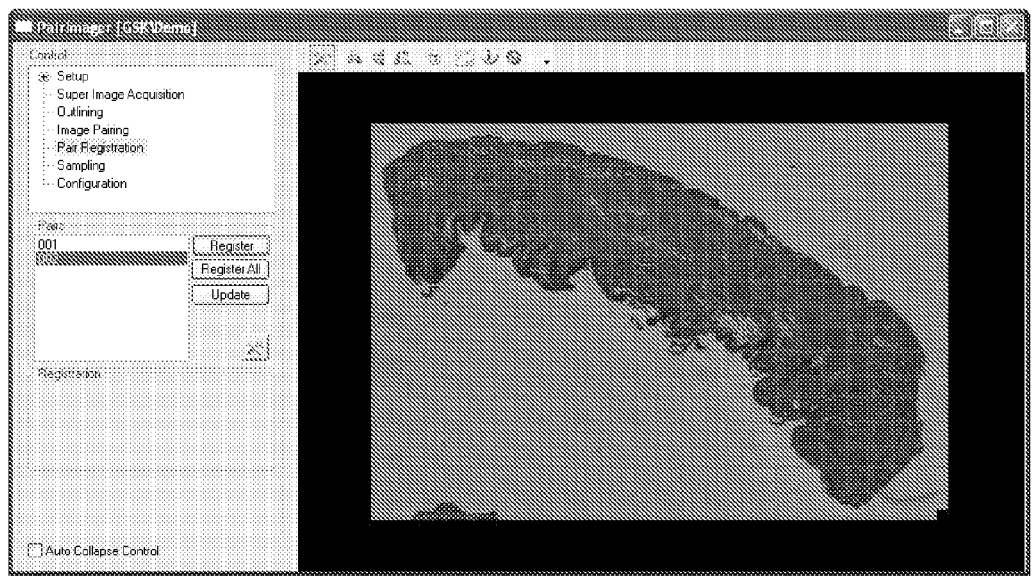
Figure 10C:
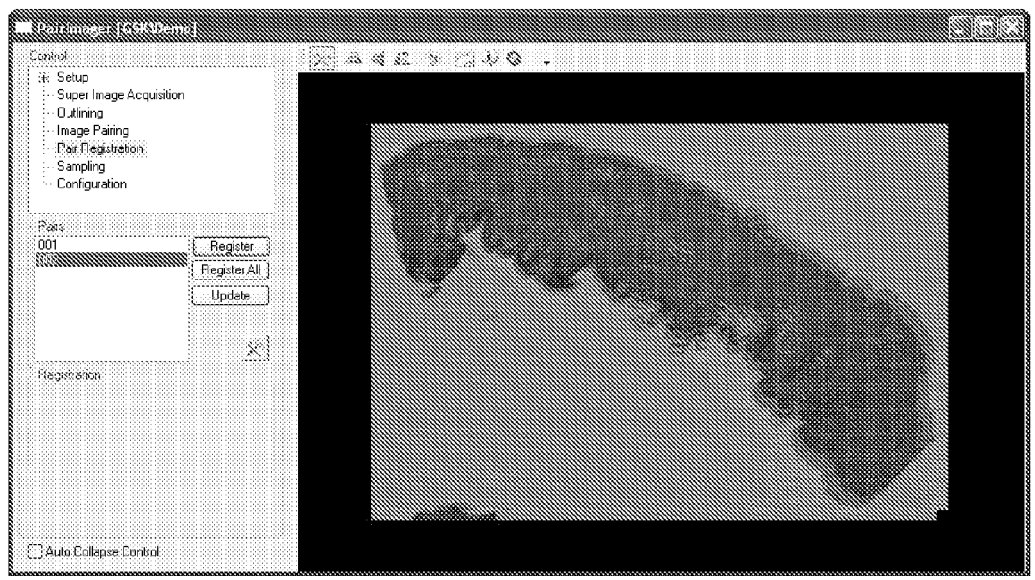
Figure 10D:
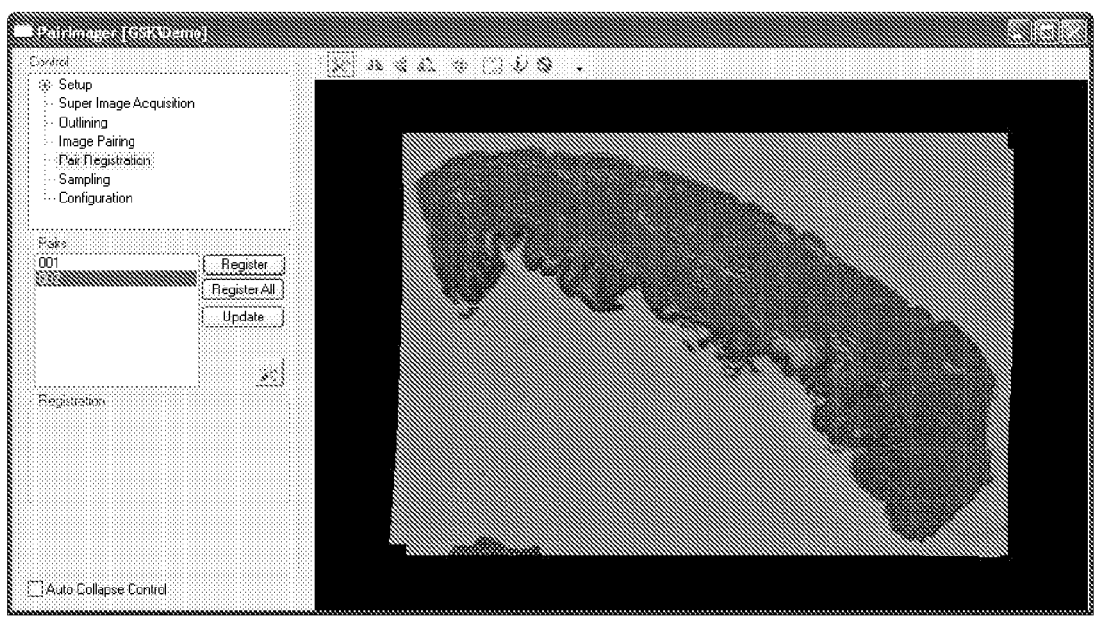

FIG. 10 shows examples of screen dumps for registration of pair 2 in FIG. 8, wherein 10a shows before registration, and 10b overlay before registration, and 10c the two sections after registration, and 10d the overlay after registration.

Figure 11:
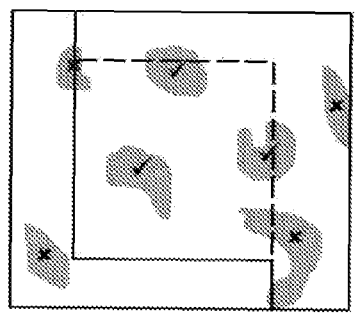

FIG. 11 shows an unbiased counting frame. An unbiased counting frame in a 2D field containing several particles. The ticked particles can be counted and the crossed particle can not.

Figure 12:
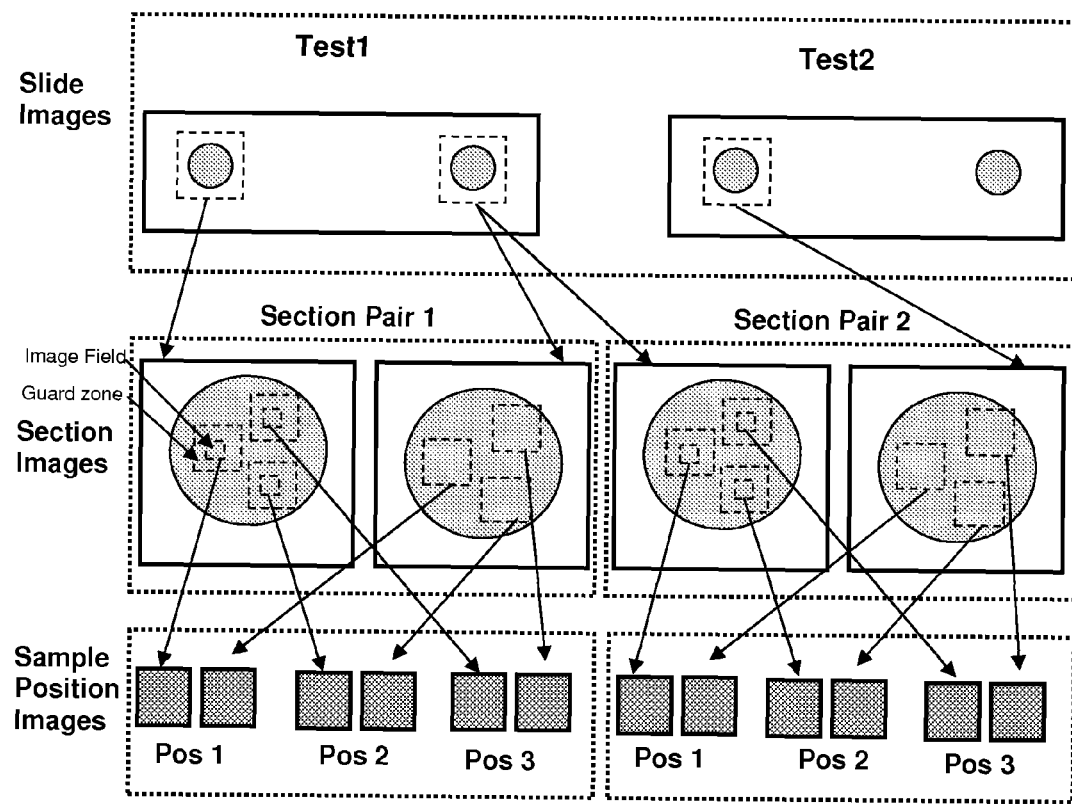

FIG. 12 shows sampling of sections on two slides discussed further in Naming Example below.

DETAILED DESCRIPTION OF THE INVENTION

Definitions:

Image registration: Image Registration is the process of transforming two digital images into one coordinate system. Registration is necessary in order to be able to compare the structures seen in the two images of a disector pair. One frequently used approach to image registration is to identify the transform (typically translation and rotation) that maximizes cross-correlation or cross-covariance between the two images.

Superimage: An image obtained at low magnification (e.g. ×2), preferably covering the entire slide and/or comprising all the image fields to be sampled. The image is typically formed by systematically acquiring semi-overlapping Fields Of View (FOV) covering the entire specimen and stitching these images together.

Object type: The type of object quantified, such as one or more type of cells, as well as other structures in the image, such as vessels.

Mask: A mask defines an area or Region Of Interest (ROI) in an image. For each image several such masks may be defined. In VIS, masks have unique numbers.

Field Of View (FOV): The part of a given section seen through the microscope.

Adjacent: Adjacent sections may or may not imply contact between sections, but always implies that it is the shortest distance allowing for a meaningful recognition of the structures through which the sections are obtained. As a rule of thumb, the distance between two adjacent sections should be small compared to the size of the objects/structures of interest.

Section: A section is a slice of the specimen to be analysed, in a preferred embodiment a section is a histological section, wherein histological sections are thin slices of tissue applied to a microscopic slide, for example around 5 to 10 micrometres thick, which are viewed under a microscope.

Look-up image/reference image: a corresponding image pair, one is called the reference image and the other the look-up image depending on which image is designated to be the reference image.

Corresponding image pair: This term is used for describing images, either two or more individual fields of view or a number of fields of views that are stitched together, in the reference- and lookup sections that are depicting essentially the same structures, although in different sections. The corresponding image pair may or may not be perfectly registered, but it is a requirement that all structures visible in the reference image are essentially covered in the lookup image.

Counting event: All objects/structures that are visible in the reference image but not in the corresponding lookup image are considered counting events.

Image field: An "image field" is any arbitrary informative region across which an informative quantitative analysis can be carried out. In some instances, an image field is a microscopic field of view at low magnification (e.g. 1.25×-2×). An entire microscope field of view can then be used for the image capturing and analysis at 40×-100× magnification for analysis. Another example of an image field is an area which is selected for a specific analysis.

Guard zone: A zone around the image field in section A or B, that ensures that the correct corresponding image field to the image field in section A is fully contained in the image region acquired in section B.

Offline: The present invention allows for offline quantification of the objects in the image, wherein offline means that the quantification process is conducted on images saved on a memory medium, such as a hard disk, and not during acquisition of the image.

Method for Obtaining at Least One Corresponding Image Pair

In a first aspect, the present invention relates to a method for obtaining at least one corresponding image pair from at least two adjacent sections A and B of a specimen, said method comprising the steps of:— a) obtaining a superimage of at least part of section A and a superimage of at least part of section B,
b) carrying out an image registration process on the two superimages by establishing correspondence between features of the two related superimages, in order to obtain a mathematical transformation rule,
c) identifying an image field within section A,
d) using said mathematical transformation rule to identify an area within section B, said area comprising an image field within section B corresponding to said image field within section A,
e) obtaining an image of said image field within section A identified in step c) and obtaining an image of said image field within section B identified in step d) to obtain a corresponding image pair,
f) optionally repeating steps c)-e) one or more times to obtain one or more different corresponding image pair(s) of one or more different image fields in the two sections A and B,
g) storing a digitized version of said corresponding image pair(s) in a computer-readable storage means.

Obtaining the Sections and Images

As is known by one skilled in the art, general sampling for microscopy of biological sections is hierarchical. Blocks are taken from main specimen, sections are cut from blocks, fields are examined on sections and measurements are made on fields. For the physical disector it is preferred that the distance between adjacent sections is known. These adjacent section pairs can then be marked to indicate that they are a pair. Preferably, the distance between the sections may not be longer than 30% of the size of the particles to be counted. Preferred section thicknesses are less that 4-5 µm.

The sections can for example be viewed using Brightfield microscopy, fluorescence microscopy or confocal microscopy. The images of the sections can be obtained using any suitable system known to one skilled in the art. Preferably a digital camera is used. The system used to obtain the image can optionally also use auto-focus (either software- or hardware-implemented).

For example, the microscope can include motorized stage, an automated apparatus for focussing, for changing lens objectives between high and low magnification, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, and a bar code reader for reading encoded information from the slide. An example of a microscope performing at least some of these functions is manufactured by Carl Zeiss, Inc. of Germany, Leica Microsystems, Nikon, or Olympus.

Preferably, the images obtained are monochrome images, color images, or multi-frame (e.g. multispectral) images. Images are preferably stored as TIFF images, or as JPEG or other standard formats.

In another embodiment the superimage and/or the image fields may be acquired from a virtual slide obtained by means of a virtual microscope imaging the sections in question. In this embodiment, the entire tissue area has been scanned at high magnification in e.g. a virtual slide scanner, and the resulting image is already stored on the harddisk. The system now handles this large image as if it was controlling a microscope, stage, camera etc. Thus, the user can use the exact same interface to work with virtual microscope images as when working with an actual microscope. With this approach it is possible to further automate the use of unbiased methods by, potentially, scan sections from an entire study (or several studies), and perform all subsequent operations off-line.

Specimen

Any suitable specimen can be used in the methods of the present invention. Preferably, said specimen is a biological specimen. Thus, said specimen can be a tissue sample. The specimen can also be labelled with at least one chemical marker, such as at least one fluorescent marker. In another embodiment, said specimen can have optical properties. It is preferred that the specimen is illuminated while the images are obtained, such as by using UV or illumination visible to the human eye. In one preferred embodiment, the specimen includes a plurality of cells, such as human cells, such as a plurality of human cells potentially including one or more human cancer cells, such as breast cancer cells.

Superimage

In one embodiment of the method of the present invention, the superimages are obtained using a lower resolution than the resolution used to obtain the images of step e). In another embodiment, the superimages are obtained using a magnification of ×2.5, ×4, ×5 or ×10.

It is to be understood by one skilled in the art that by the references to "two superimages" herein is also intended embodiments in which the two superimages can be comprised in one single larger superimage.

The two images may for example be acquired from conventional microscope slides or from virtual slides.

Registration

Step b) of the method concerns carrying out an image registration process on the two superimages by establishing correspondence between features of the two related superimages, in order to obtain a mathematical transformation rule.

The feature(s) used in the registration process can be any suitable feature recognised by one skilled in the art as useful in the registration process. The feature can for example be an anatomical structure, such as, but not restricted to, an anatomical structure selected from the group consisting of: the outer shape or outline of the section or specimen, vascular structure(s), nerve structure(s), muscle structure(s), cell membrane(s), space(s) in the section, cell(s), an alveolus, particle(s) or a nucleus.

The registration process itself can be carried out using any process known to one skilled in the art. For example, registration can be carried out using a method disclosed in Mainz et. al 1998 or one can use one or more of: Correlation and Sequential methods, Fourier methods or Point mapping methods. Thus, image registration of sections can for example be carried out using one or more of: spatial mapping, a geometric transformation, a combination of a spatial transformation and a gray-level interpolation. Preferred methods for gray level interpolation include for example the nearest neighbor approach, cubic convolution interpolation and bilinear interpolation.

In one preferred embodiment of the present invention, image registration comprises or consists of one or more (preferably all three) of the following:
1. Detection of tissue area in the two images belonging to the pair
2. Rigid warp of one image to fit approximately on the other.
3. Non-rigid warp based on the approximate fit, to fit the images more correctly.

For tissue detection, any method can be used. One preferred embodiment uses the VisioMorph segmentation tool, available commercially from Visiopharm NS.

The transformation rule obtained by the registration process preferably includes a rotation rule and/or a translation rule and/or a warp rule, which is carried out on at least part of the section.

Identifying an Image Field within Section A

Step c) of the method of the present invention comprises the step of identifying an image field within section A. An image field is chosen e.g. at a random location, a systematic uniformly random location, or at a user defined location.

In one embodiment of the present invention, the locations (defined e.g. as upper left corner) of the considered image field(s) represent a random sample, such as a systemic uniform random sample, based on the reference section and the corresponding locations in the lookup section. In another embodiment of the present invention, the considered image field(s) represent semi-random sample. In another embodiment of the present invention, the first image field is identified at random and the subsequent image fields are identified using a pre-defined function. In another embodiment of the present invention, one or more of the considered image field(s) can be selected in the specimen by a human operator, such as by using a computer mouse. Sampling principles are described in e.g. [Howard & Reed].

When sampling, every part of the original specimen should have the same chance of becoming part of the final sample on which measurements are to be made. Thus, it can in one embodiment be advantageous to apply systematic uniform random sampling at every level of the sampling hierarchy.

Identifying an Image Field within Section B

Step d) of the method of the present invention comprises the step of using said mathematical transformation rule to identify an area within section B, said area comprising an image field within section B corresponding to said image field within section A. It is preferred that the image field within section B comprises an area corresponding to the image field within section A together with a guard zone around said area in section B. The presence of this guard zone has been found by the inventors of the present invention be preferred for realizing the invention. Preferably, the minimum guard zone added to each border of said area in step d) is calculated using the following formula:

$$\frac{(\text{working magnification of said area in step } d)}{(superimage\ B\ \text{magnification})} \times$$

(margin of registration error of *superimage B* in pixels)

For example, the area of said area in step d) can be at least 1.1 times the area of said image field within section A, such as at least 1.2 times the area of said image field within section A, for example at least 1.3 times the area of said image field within section A, such as at least 1.4 times the area of said image field within section A, for example at least 1.5 times the area of said image field within section A, such as at least 1.6 times the area of said image field within section A, for example at least 1.7 times the area of said image field within section A, such as at least 1.8 times the area of said image field within section A, such as at least 1.9 times the area of said image field within section A, such as at least 2.0 times the area of said image field within section A, such as at least 2.5 times the area of said image field within section A, such as at least 3.0 times the area of said image field within section A, such as at least 3.5 times the area of said image field within section A, such as at least 4.0 times the area of said image field within section A, such as at least 4.5 times the area of said image field within section A, such as at least 5.0 times the area of said image field within section A, such as at least 6.0 times the area of said image field within section A, such as at least 7.0 times the area of said image field within section A, such as at least 8.0 times the area of said image field within section A, such as at least 9.0 times the area of said image field within section A, such as at least 10 times the area of said image field within section A.

In another embodiment a guard zone is also selected for the image field in section A. Thereby larger image areas may be compared when performing a second registration process, than if only the image fields are compared, thereby increasing the robustness of the second registration.

Area of Image Pairs Taken

For the methods according to the present invention, it is preferred that the total area for all the image pairs taken is at least 0.5% of the area of the section analysed, such as at least 1%, for example at least 2%, such as at least 5%, for example at least 8%, such as at least 10%, for example at least 15%, such as at feast 20%, for example at least 25%, such as at least 30%, for example at least 35%, such as at least 40%, for example at least 50%.

Further Optional Method Steps

The methods of the present invention further optionally comprise step f), which relates to repeating steps c)-e) one or more times to obtain one or more different corresponding image pair(s) of one or more different image fields in the two sections A and B, Step f) can be repeated to obtain at least two image pairs, such as at least three, for example at least four, such as at least five, for example at least six, such as at least seven, for example at least eight, such as at least nine, for example at least ten, such as at least 15, for example at least 20, such as at least 25, for example at least 50.

After the images are obtained using the method of the present invention, it is preferred that they are stored in a digitized version of said corresponding image pair(s) in a computer-readable storage means.

Another optional step in the methods of the present invention comprises carrying out the additional step of carrying out a second registration process on the two images obtained in step e) to obtain a registered corresponding image pair. This allows optimal registration and may be carried out using any registration process, such as any of the registration process described herein. Preferably, said registration process is as described in A Survey of Medical Image Registration (9).

The method of the present invention can also comprise the additional step of automatically determining a conclusion from the results of the method, such as a pharmacological conclusion. One preferred conclusion can for example be a conclusion relating to the proliferative index of an organ or tumor, such as a number representing an estimate of the relative number of proliferating cells, optionally with a value indicating the statistical accuracy of said number.

The method of the present invention may be carried out for any type of specimen, such as a histological section of a variety of organs, such as kidneys, lungs, liver, muscle, uterus, bone, heart, fat tissue, and gastrointestinal tissue.

In a preferred embodiment of the present invention, the method further comprises the additional step of automatically presenting a report, and optionally one or more digital image(s), on a graphical user interface.

The methods of the present invention are preferably automated or semi-automated. In the following table the steps that may be carried out automated (AUTO) or optionally automated (OPTIONALLY AUTO) are listed:

|  | Step |
| --- | --- |
| AUTO: | Creation of superimages by stitching |
| OPTIONALLY AUTO: | Segmentation of tissue sections |
| OPTIONALLY AUTO: | Registration of super images |
| AUTO: | Sampling of image pairs at working resolution (employing auto-focus, auto white balance, auto exposure) |
| OPTIONALLY AUTO: | Fine-registration of corresponding image pairs |
| AUTO: | Recording of user-demarcated counting events |

In one embodiment of the present invention, any of the methods described herein can be carried out for at least one, two or three different object types, such as for different cell or tissue types and/or different cell structures.

The methods according to the present invention can further comprise the aspect of using a computer readable medium having stored therein instructions for causing one or more processors to execute the steps of the method.

Method for Assessing at Least Two Adjacent Sections of a Specimen

In another aspect, the present invention provides a method for assessing at least two adjacent sections of a specimen. Said method comprises the steps of:— i) providing at least one corresponding image pair according to any of the methods disclosed above, ii) identifying the counting events for at least one type of object on said image fields within at least one corresponding image pair, optionally using automatic means.

Said method for assessing at least two adjacent sections can also comprise the additional step of:

quantifying the amount or number of said counting events on the images of said image field(s) within section A and said image field(s) within section B. Said quantification can include e.g. calculating the number of counting events and/or objects per volume of tissue, such as calculating an estimate of the number of counting events and/or objects in the total specimen volume together with a confidence interval. Said quantification can also optionally include the use of an unbiased counting frame. In one embodiment of the present invention, the quantification entails that at least one human operator marks the specific counting events, preferably on a computer interface, such as using a computer mouse. Preferably, the quantification is carried out using an estimator, such as e.g Cavalieris Unbiased Estimator of Volume. Preferably, the quantification process occurs offline.

In another embodiment the quantification step may be assisted by having the system present to the human operator suggested counting events, by for example applying a mark or a label to each suggested counting event in the image. In order to automatically identify suggested counting events in the image, image analysis may be performed of the analyzed image field pairs.

The method according to the present invention for assessing at least two adjacent sections can be carried out for at least two different image fields within the sections, such as for at least three different image fields within the sections, for example for at least four different image fields within the sections, such as for at least five different image fields within the sections, for example for at least six different image fields within the sections, such as for at least seven different image fields within the sections, for example for at least eight different image fields within the sections, such as for at least nine different image fields within the sections, for example for at least ten different image fields within the sections, such as for at least twenty different image fields within the sections; and preferably furthermore wherein the amount or quantity of all the counting events from all the image fields analysed is obtained.

PREFERRED EMBODIMENTS

Preferably, one or more of the following is used in the methods of the present invention:

(i) Automated Sampling

Having identified one or more tissue regions on the slide, preferably using the superimage(s), a further step in the method of the present invention is sampling in order to generate images of one or more image field(s) within sections A and B, and optionally further image pairs. This can be done in several ways, depending upon the application:

1. Exhaustive imaging of each identified image field within the slide, with one or more images per image field. In the latter case, the total image may be produced by stitching of image tiles. Due to lack of perfect alignment (and precision) of standard motorized stages, a cross-correlation based image alignment will often be required as a post-processing step. The images of each image field are stored in the database under a study name, study unit, and measurement as defined by the bar-code on the slide. The applications of this range from Tissue Micro Arrays to exhaustive scanning of entire slides (for subsequent viewing and qualitative/quantitative assessment and interpretation).

2. Sampling of two regions: This is a special, but frequently occurring situation, when using the physical disector. Here, the two sections are outlined, and image analysis is used to automatically obtain a perfect registration of the two sections. Subsequently, two image stacks (reference and look-up) are obtained using systematic random sampling of image fields in the two aligned sections.

3. Sampling over several sections is useful when e.g. a smooth fractionator has been used to obtain several tissue sections that are placed together in some embedding material and the entire volume is subsequently sectioned. Here, the system should be able to determine a sampling region that encompasses all image fields simultaneously. If image fields are sampled between tissue sections, it should be simple (using image analysis) to recognize this fact, and omit storage of images related to this field.

The imaging carried out during the sampling is preferably automated, such as comprising one or more of the following: Auto-focus, Auto-exposure and Auto-white balance (ii) Image Segmentation:

Image segmentation is the process of splitting an image into spatially well-defined regions or objects belonging to tissue or object classes of relevance to a specific application. Based on the segmented image, information such as number of objects, area, circumference etc can be measured. Thus, image segmentation is useful for the subsequent extraction of information from the image. Preferred methods for image segmentation include, but are not restricted to Thresholding, Bayesian Classification and K-Means clustering.

(iii) Disector Configuration

Various disector configurations known to one skilled in the art can be used. Parameters will depend upon the specific application, and can in one embodiment be stored in a configuration which can for example only be set up and modified by an administrator. Such parameters can e.g. include, but are not limited to, the following:

Objective for acquiring Superimages
Objective for acquiring intermediate resolution images
Objective for working resolution
Settings for condenser, filters etc for each of the objectives
Application specific metric for "goodness-of-registration"
Size of counting frame (iv) Quantifying Counting Events Objects, represented by counting events, are preferably quantified using an unbiased counting frame (see above).

To get the estimation of the total number of objects in the whole specimen, the fractionator principle can be used (see e.g. Howard & Reed). The principle of the fractionator is to take a known fraction, 1/x, of the whole specimen and count all objects, n, in that fraction, preferably using an unbiased counting frame. The unbiased estimate of the total number of particles in the whole object is then given by n times x.

Although a human operator can in one embodiment act to quantify the counting events—either partially by clicking on the events using a mouse or by manually counting the events, another embodiment of the present invention enables counting events to be counted using a signal counting device, such as e.g. VisioMorph.

Furthermore, assisted counting wherein suggested counting events are presented to the operator as described above, is also envisaged.

Computer Readable Medium

In another aspect, the present invention further encompasses a computer readable medium comprising instructions for carrying out one or more of the methods disclosed herein. Suitable computer-readable media can for example be a hard disk to provide storage of data, data structures, computer-executable instructions, and the like. Other types of media which are readable by a computer, such as removable magnetic disks, CDs, magnetic cassettes, flash memory cards, digital video disks, and the like, may also be used.

Automated System

In another aspect, the present invention further encompasses an automated or semi-automated system suitable for carrying out one or more of the methods disclosed herein, said automated or semi-automated system comprising, in combination:

a database capable of including a plurality of digital images of a plurality of biological specimens;
a software module for analyzing a plurality of pixels from a digital image of a biological specimen;
a control module comprising instructions for carrying out said method(s).

Said automated or semi-automated system can also further comprise one or more of: a slide loader, a barcode reader, a microscope (preferably motorized), and a stage (preferably motorized).

Several automated slide loaders are commercially available today, allowing for the automated loading of slides onto a motorized stage mounted on a microscope. Suitable systems are e.g. supplied by Olympus or TrestleCorp. Such loaders can be integrated to standard Windows based computers, have the ability to hold 100+ slides, and read a range of bar-code symbologies.

Integrating such a loader with the system allows unattended, high-volume sampling and digitization of microscopy slides, and with the application of bar-codes data management at a very high level can be fully integrated into the work process.

Often one slide may contain several tissue sections. The methods of the present invention can thus be used as a type of physical dissector, where e.g. at least two adjacent sections from the specimen are placed side by side on the slide.

The system according to the present invention may also include a linear encoder for z-axis control.

Using a fully automated microscope, it is possible to let the system switch between low and high magnification. By using low magnification, it is possible to obtain a "superlens" image providing an overview of the entire slide, and let the system automatically identify regions on the slide containing tissue, using image analysis.

The system may include an image processor and digitizer, and a general processor with peripherals for printing, storage, etc. The general processor can be an INTEL PENTIUM microprocessor or similar microprocessor based microcomputer, although it may be another computer-type device suitable for efficient execution of the functions described herein. The general processor can for example control the functioning and the flow of data between components of the device, may cause execution of additional primary feature signal counting algorithms, and handles the storage of image and classification information. The general processor can additionally control peripheral devices such as a printer, a storage device, such as an optical or magnetic hard disk, a tape drive, etc., as well as other devices including a bar code reader, a slide marker, autofocus circuitry, a robotic slide handler, the stage, and a mouse.

The image processor and digitizer preferably act to digitize images from the digital camera and can optionally performs a primary algorithmic classification on the images to filter out unwanted information. The image processor and the general computer may each access read-only and/or random access memory, as would be readily apparent to one skilled in the art, for the storage and execution of software necessary to perform the functions described relative to that processing component. Further, each component and includes circuitry, integrated circuit chips, etc. for the control of communication or data transfer over the data bus, as well as other functions typical of similar processors.

The system can additionally provide an opportunity for a user to provide guidance during the entity quantification process. For example, the user can specify a particular area of interest by selecting it on the screen. Typically, the super image is presented, and the user may select an area or areas via a pointing device (e.g., a mouse). Counting is then limited to only the selected area or areas. Such a feature can be particularly useful when the user recognizes that a certain area of the image relates to an image field of interest.

The system can also provide a way to eliminate a specified area or areas selected via a pointing device (e.g., a mouse). Portions of the image within the specified area or areas (sometimes called "gated areas") is ignored when spots are counted.

Applications

The methods according to the present invention can be used in a number of applications. In a preferred embodiment the methods are used in histology, such as histology used in both discovery and safety pharmacology. For example, one can use the methods of the present invention to accurately estimate the mass, volume and number of Beta-cells in a biological specimen. In another embodiment, one can use the methods of the present invention to accurately estimate the number, volume, and size distribution of alveoli in a biological specimen. In another embodiment, one can use the methods of the present invention to accurately estimate cell proliferations and apoptosis in a biological specimen. Tissues that can be investigated using the methods of the present invention include, but are not restricted to, liver, lung, lymph (for e.g. immuno toxicity assays), or thyroid glands. The methods can also be used in analyses of reproductive toxicology.

In another embodiment of the present invention, the methods of the present invention can be used in developmental neurotoxicity studies. The developing brain can be affected by neurotoxic agents either as a primary target or indirectly. Developmental injuries often manifest themselves as subtle quantitative changes in cell numbers. Unbiased stereological determination of a neuron using the methods of the present invention can assist in the elucidation of potential effects of developmental neurotoxicants: one can thus study the numbers of neurons as a potential new end-point in regulatory developing neurotoxicity testing, using the methods of the present invention.

DETAILED DESCRIPTION OF THE DRAWINGS

References

References disclosing aspects suitable for use in the methods of the present invention are as follows:—

[1] G. H Granlund, H. Knutsson (1995), Signal processing for computer vision, Dordrecht, Kluwer Academic Publishers. ISBN 0-7923-9530-1.

[2] C.V. Howard, M. G. Reed (1998), Unbiased Stereology Three dimensional measurements in microscopy, Oxford, BIOS Scientific Publishers. ISBN 1 85996 071 5
[3] B. Srinivasa Reddy, B. N. Chatterji (1996), An FFT-based technique for translation, rotation and scale invariant image registration. IEEE Transactions on Image Processing, 5(8) 1266-1271.
[4] P. R. Mouton (2002), Principles and Practices of Unbiased Stereology: An Introduction for Bioscientists. Baltimore, Md., USA: The Johns Hopkins University Press, p 9.
[5] B. Zitov'a, J. Flusser (2003), Image registration methods: a survey. Image and Vision Computing, 21 977-1000.
[6] L. Gottesfield Brown (1992), A survey of image registration techniques. ACM Computing Surveys, 24(4) 325-376.
[7] I. Pitas (2000), Digital image processing algorithms and applications, John Wiley & Sons, Inc. ISBN 0 471 37739 2
[8] R. C. Gonzalez, R. E. Woods, Digital Image Processing, Upper Saddle River, N.J., Prentice Hall, Inc. ISBN 0-201-18075-8
[9] J. B: Antoine Mainz and Max A. Viergever, A Survey of Medical Image Registration, Medical Image Analysis (1998), Volume 2, pp 1-37.

EXAMPLES

Example 1

Image Acquisition

In one embodiment of the present invention, in order to make acquisition of disector pairs happen in an automated way, the system can run in two modes: the Preparation Mode and the Image Sampling mode. Examples of these modes are described below.

1. Preparation Mode

| Req. | Description |
| --- | --- |
| 1.1 | The operator loads the appropriate Disector configuration |
| 1.2 | The operator is loading the specimen holder with up to eight (8) slides. The system requires operator-input regarding: STUDY ID Number of loaded slides in the specimen holder |
| 1.4 | The system acquires Superimages for all loaded slides, according to the loaded disector configuration. Note: The system is equipped with auto white balance and auto-exposure in order to ensure optimal image quality |
| 1.5 | For each of the acquired superimages, the operator outlines the individual sections using masks. For each superimage, the user-defined masks have unique identifiers (e.g. a number). |
| 1.6 | When this process is completed, the system performs a first registration of all defined disector pairs based on pertinent the superimages. This will create a first rough registration that will be an important basis for a far more accurate registration at a higher resolution at a later stage in the process. Through the development process, the quality of this first crude registration will become known. Typically an accuracy of 1-2 pixels can be achieved. Note that this will translate into a larger, but known, error in a larger magnification. Hence, the process following from this point will be concerned with incremental improvements of the registration. |
| 1.7 | The operator has to approve the initial crude registration of all disector pairs. This initial registration can be modified manually by the operator, in order to assure that the basis for the subsequent high-level registration and image sampling is correct. |
| 1.8 | When all disector pairs has been registered in the superimage resolution, the system is ready for sampling mode. |

2. Image Sampling and Registration Mode

The steps described in the following are all running unattended.

2.1 Automated Refinement of Registration

It may turn out that this step can be omitted from some practical user applications.

| Req. | Description |
| --- | --- |
| 2.1.1 | The system automatically defines the outline (or meander) of each reference section for every disector pair. |
| 2.1.2 | Based on the information in the Disector configuration, the system automatically changes the objective to medium magnification (e.g. xIO magnification). |
| 2.1.3 | Fields Of View are sampled arbitrarily from the Reference section (R-FOV) for each given disector pair at medium resolution. Corresponding fields are found in the lookup section (L-FOV). For each corresponding R-FOV and L-. FOV a registration is carried out. |
| 2.1.4 | Based on the registration information obtained from the medium resolution images, the initial registration is further refined and updated. The resulting registration is used in the high resolution sampling described below. |

2.2 High-Resolution Sampling and Registration

| Req. | Description |
| --- | --- |
| 2.2.1 | The system automatically selects the objective corresponding to the (high) working resolution. |
| 2.2.2 | Using the Systematic random Sampling principle, the meander detected for each reference section, and the improved registration, the system now automatically identifies matching R-FOV and L-FOV images at full resolution. Based on the estimated image registration accuracy, the L-FOV is deliberately made sufficiently large (expanded) for ensuring that the R-FOV is fully matched/registered within this image. |
| 2.2.3 | Both R-FOV and L-FOV images are acquired and the final registration is computed. |

3. Data Management

| Req. | Description |
|---|---|
| 3.1 | All registered disector pairs L-FOV and R-FOV, acquired as described under section 2.2, are automatically stored in the database under the appropriate study and study unit as an integrated part of the image acquisition and registration process. |
| 3.2 | The Superimage related to a given disector pair is stored in the VIS database under the relevant study and study unit ID. |
| 3.3 | Offline, after image acquisition has been completed, the operator can locate and bring up any given disector pair for analysis and quantification. |

Example 2

Example of Image Quantification

Quantification can be carried out manually based on stereological principles, and can e.g. be carried out using a variety of software, such as newCAST. (Visiopharm A/S).

| Req. | Description |
|---|---|
| 1.1 | Starting in quantification mode, the system will automatically take the operator though the entire study going through slide-by-slide and FOV-by-FOV. |
| 1.2 | Disector pairs are presented to the operator with the counting frame overlaid the registered images. |
| 1.3 | The quality of the registration can be inspected in viewing mode, allowing the operator to overlay the two images in a separate window. The transparency of the top image can be altered. The overlay viewing capability should aid the user in identifying counting event. |
| 1.4 | Counted events are stored and treated as usual in the newCAST system. |

Example 3

Example of General System Specification

Motorized microscope: Nikon 90i Objectives: ×2, ×IO (dry), ×20 (dry+oil), and ×40 (dry+oil) Camera outlet: c-mount Digital camera: Olympus DP70 Motorized stage: Prior H138 Specimen holder: 8-slides The system is capable of handling multiple sections per slide.

The system includes motorized stage with a specimen holder capable of holding up to eight slides. The Physical Disector modules are implemented and integrated on the VIS/newCAST platform, available commercially from Visiopharm A/S.

Example 4

Example of an Image Acquisition, Registration and Sampling

The image acquisition, registration and sampling may be carried out as described by the below work flow.
I: Start Visiopharm Integrator System (VIS)
1) Launch VIS (from the VIS icon on the desktop or Start menu |Programs|Visiopharm|VIS).
II: Recording Sample Images
1) Launch VIS (from the VIS icon on the desktop or Start menu |Programs|Visiopharm|VIS)
2) Open the Acquisition module.
3) Above the Launch button, Select AutomatedPhysicalDisector in the list.
4) Press the Launch button to open the automated physical disector dialog.
5) Select the Configurations page.
 a) Select the correct configuration.
 b) Press load button to load the configuration.
6) Select the 'Super Image' page.
 a) Under Super Images to capture, choose how many slides should be imaged.
7) Press the Start button. This starts the live view in the VIS window, and launches the ROI capture wizard dialog. Step through the wizard as described below.
 a) Check the Apply flat field correction box.
 b) Press Next>>.
 c) Ensure that the live image is in focus and correctly illuminated.
 d) Press Next>>.
 e) Use the joystick to move to a position on the slide where no tissue is seen, and where excess staining and other background variation is kept to a minimum.
 f) Press Next>>.
 g) The super Images are acquired automatically. Wait until acquisition has finished.
8) Select the Outlining page.
 a) Press classify button to launch the classification dialog.
 b) Ensure that the correct classification is selected.
 c) Press classify button again to segment the visible super image into tissue and background.
 d) Or press classify button to segment all super images in the list.
9) Select the Image Pairing page. Tissue sections are now displayed with boxes around them.
 a) Left click on the first section in a pair.
 b) Left click on the second section in a pair.
 c) The pair is added to the list.
 d) Repeat above for all section pairs.
 e) Select a pair in the list and press Rename to change the pair name.
 f) Select a pair in the list and press Delete to delete the selected pair.
 g) If all pairs should be redefined, press Reset to delete all pairs and replace the section boxes.
10) Select the Pair Registration page.
 a) Select a pair in the list.
 b) Press Register to match the two sections in the pair.
 c) Or press Register All to match all sections pairs in the list.
11) Select the Sampling page.
 a) Select a pair in the list.
 b) Press sample button to do a sampling in the selected pair.
 c) Or press sample all button to do a sampling in all pairs in the list.
12) The Specify Sampling Name dialog is shown.
 a) Write an ID name for the current sampling. Several samplings can be done on the same pair as long as they have different sampling IDs.
 b) Press OK.
13) The Automated Save dialog is shown.
 a) Specify where to store the sample images in the database. Only the two upper layers can be specified by the user, the third level will be automatically chosen based on the pair name and sampling ID.
 b) Press Enable.

14) The ROI capture wizard dialog is launched. Step through the wizard as described below.
   a) Check the Apply flat field correction box.
   b) Press Next>>.
   c) Ensure that the live image is in focus and correctly illuminated.
   d) Press Next>>.
   e) Use the joystick to move to a position on the slide where no tissue is seen, and where excess staining and other background variation is kept to a minimum.
   f) Press Next>>.
   g) The sample images are acquired automatically. Wait until acquisition has finished.
15) Select the Image approval page.
   a) Select the first image in the list. Verify that the image quality is ok.
   b) If the image quality is not ok, press Retake. This launches the ROI capture wizard and allows a retake of the current image.
   c) Use the Down arrow key to step through the list of images and ensure that all images are ok.
16) If all sampling has finished, close down the physical dissector.

III: Counting Sampled Images
1) in VIS open the newCAST module.
2) in the database, choose the measurement (third level) where the sampled images have been stored.
3) Press offline counting button to start a counting on the sampled images. This launches the Offline sampling setup dialog.
   a) Choose the sampling which should be counted.
4) The paired samples are shown side by side in a split screen view.
5) Press basic view button to select Basic imaging view mode that allows you to move the right image around.
6) If counting frames are used, click and hold left mouse button in the right image and drag the right image around until corresponding areas are seen inside the two counting frames.
7) Press count button to select the Count Tool mode that allows you to add count marks on the images.
8) Count the relevant events in the paired samples. Counts can be done in either of the two windows.
9) Press next button to go to the next sampling position.
10) Press prey button to go to the previous sampling position.
11) If the last sample has already been reached, pressing next button will launch the Meander sampling box.
   a) Press Finish to end the counting.
   b) Or press Repeat to start counting again from the first sample. Old counts will not be deleted.
12) Press measurement view button to open Data: View measurement Data. Select the different headings to the left to show corresponding data. The Quantities heading will show the counts made during sampling.
13) Press study view button to open Data: View study data. Select the first measurement in the study unit (level 2) of the database to show the total of all saved measurements.
14) When leaving the module or selecting a new measurement in the database a save dialog might appear depending on the settings of Data saving automation in the File|Preferences menu.

Example 5

Example Illustrating how Images can be Saved in a Database

Slide Image Naming

The image naming convention should preferably ensure that an alphabetic listing of the images shows pairs and paired sample positions consecutively. For each image acquisition session, a number of slides are imaged. These are stored in the database as measurements with the name:
"Slide_ID"
   ID. A user defined name describing the slide.

Paired Section Image Naming
   On each slide a number of tissue sections are seen. These sections are paired and the pairs may be placed on the same slide or on different slides. The paired section images are registered and stored in the database as measurements with the names:
"PairN__1_ID"
"PairN__2_ID"
   N. The number of the current section pair. This number is unique under the current study unit.
   1 and 2. The number describing if it is the first or second image of the pair.
   ID. A user defined name describing the slide.

Paired Sample Position Name
   For each section, a number of corresponding positions in are imaged for each section pair. The paired sample position images are registered and stored in the database as measurements with the names:
"PairN_PosM__1_D"
"PairN_PosM__2_ID"
   N. The number of the current section pair. This number is specific under the current study unit.
   M. The number of the current sample position in section pair N. This number is specific under the current section pair.
   1 and 2. The number describing if it is the first or second image of the pair.
   ID. A user defined name describing the slide.

Naming Example

The following example shows sampling of sections on two slides with reference to FIG. 12.
The slides area named "Test1" and "Test2" by the user. Two section pairs are found in the slides. One is on the same slide and one is on different slides. In each section pair, three positions are sampled. Due to registration uncertainty, a larger area is imaged for the second image of each pair.
In the database, the corresponding measurement names will be:
Slide images:
   Slide_Test1
   Slide_Test2
Section images:
   Pair1__1_Test1
   Pair1__2_Test1
   Pair2__1_Test1
   Pair2__2_Test2
Sample position images:
   Pair1_Pos1__1_Test1
   Pair1_Pos1__2_Test1
   Pair1_Pos2__1_Test1
   Pair1_Pos2__2_Test1

Pair1_Pos3__1_Test1
Pair1_Pos3__2_Test1
Pair2_Pos1__1_Test1
Pair2_Pos1__2_Test2
Pair2_Pos2__1_Test1
Pair2_Pos2__2_Test2
Pair2_Pos3__1_Test1
Pair2_Pos3__2_Test2

Example 6

Example of a Two-Step Registration Process

1) Registration with Rigid Warp

Represent tissue sections as two binary images (pixel values 0 for background, 1 for object).

Calculate center of mass (CoM) of the two binary objects.

$$\text{Spatial moment } m_{pq} = \sum_i \sum_j i^p j^q f(i, j)$$

$$x_c = \frac{m_{01}}{m_{00}}, \ y_c = \frac{m_{10}}{m_{00}}$$

$$CoM = (x_c, y_c)$$

Calculate translation as difference in CoM.

Measure distance to object border from CoM as a function of sample angle for both objects. Sample at equidistant angles to create two digital signals Calculate displacement of one signal which minimizes the sum of squared differences (SSD) between the signals s1 and s2.

$$\text{For displacement } d: \ SSD_d = \sum_n (s_1(n) - s_2(n))^2$$

Use the calculated displacement to calculate the rotation between images.

Translate and rotate image 2 using an image transformation matrix to fit the tissue sections on top of each other. For rotation $\theta$ and translation $(T_x, T_y)$, the transformation matrix for each image pixel is:

$$[x' \ y' \ 1] = \begin{bmatrix} \cos(\theta) & -\sin(\theta) & 0 \\ \sin(\theta) & \cos(\theta) & 0 \\ T_x & T_y & 1 \end{bmatrix} \begin{bmatrix} x \\ y \\ 1 \end{bmatrix}$$

2) Registration with Non-Rigid Warp

Use the images which have already been registered with rigid warp.

Define equidistantly spaced search areas inside tissue section in Image 1.

Inside each search area, detect the position of maximum pixel intensity variance.

Compare small area around this position with Image 2 to find areas of maximum covariance. Collect matching positions from the search areas in a list of match points.

From the N match points, create the normal equations:

$$\begin{bmatrix} x'_1 \\ M \\ x_N \end{bmatrix} = \begin{bmatrix} 1 & f_1(x_1, y_1) & \Lambda & f_M(x_1, y_1) \\ M & M & \Lambda & M \\ 1 & f_1(x_N, y_N) & \Lambda & f_M(x_N, y_N) \end{bmatrix} \begin{bmatrix} \alpha_{x1} \\ M \\ \alpha_{xM} \end{bmatrix} + \begin{bmatrix} \varepsilon_1 \\ M \\ \varepsilon_N \end{bmatrix}$$

$$\begin{bmatrix} y'_1 \\ M \\ y_N \end{bmatrix} = \begin{bmatrix} 1 & f_1(x_1, y_1) & \Lambda & f_M(x_1, y_1) \\ M & M & \Lambda & M \\ 1 & f_1(x_N, y_N) & \Lambda & f_M(x_N, y_N) \end{bmatrix} \begin{bmatrix} \alpha_{y1} \\ M \\ \alpha_{yM} \end{bmatrix} + \begin{bmatrix} \varepsilon_1 \\ M \\ \varepsilon_N \end{bmatrix},$$

where M is the number of different functions e.g. x, y, $x^2$, $x^2$, xy, which are used for the estimation.

Use a least squares estimation to calculate the $\alpha$ parameters, resulting in the following transformation matrix for each image pixels:

$$\begin{bmatrix} x' \\ y' \end{bmatrix} = \begin{bmatrix} \alpha_{x1} & \Lambda & \alpha_{xM} \\ \alpha_{y1} & \Lambda & \alpha_{yM} \end{bmatrix} \begin{bmatrix} 1 \\ f_1(x, y) \\ M \\ f_M(x, y) \end{bmatrix}$$

Paired Sampling

When a sampling position has been determined in the first section of the pair, combine the rigid and none-rigid transformation to calculate the corresponding sampling position in the second section of the pair.

Capture high resolution sample images of the imaged specimen at the two positions. Capture a larger area for sample 2, to ensure that the area found in sample 1 can also be found in sample 2.

Use the rotation calculated for the rigid warp to rotate sample image 2.

The invention claimed is:

1. A method for obtaining at least one corresponding image pair from at least two adjacent sections A and B of a specimen, said method comprising the steps of:
   a) obtaining a superimage of at least part of section A and a superimage of at least part of section B, wherein a superimage is an image of a section comprising all image fields and an image field is an area of the image to be analysed;
   b) carrying out an image registration process on the two superimages by establishing correspondence between features of the two related superimages, so as to obtain a mathematical transformation rule,
   c) identifying an image field within section A;
   d) using said mathematical transformation rule to identify an area within section B, said area comprising an image field within section B corresponding to said image field within section A, and adding a minimum guard zone to each border of said area in section B;
   e) obtaining an image of said image field within section A identified in step c) and obtaining an image of said image field within section B identified in step d) and carrying out a second registration process on the two images to obtain a registered corresponding image pair;
   f) optionally repeating steps c)-e) one or more times to obtain one or more different corresponding image pair (s) of one or more different image fields in the two sections A and B;
   g) storing a digitized version of said registered corresponding image pair(s) in a non-transitory computer-readable storage medium; and wherein the superimages of step a) are obtained using a lower resolution than the resolution used to obtain the images of step e).

2. The method according to claim 1, wherein the superimages are obtained using a magnification of at least 2.5×.

3. The method according to claim 1, wherein the minimum guard zone is calculated using the following formula:

$$\left(\frac{\text{working magnification of said area in step } d}{\text{superimage } B \text{ magnification}}\right) \times \left(\begin{array}{l}\text{margin of registration error} \\ \text{of superimage } B \text{ in pixels}\end{array}\right)$$

wherein the area of said area in step d) is at least 1.5 times the area of said image field within section B.

4. The method according to claim 1, wherein a guard zone is also added to each border of the image field within section A.

5. The method according to claim 4, comprising the additional step of carrying out a second registration process on the two corresponding image fields and guard zones obtained in step d) to obtain a registered corresponding image pair.

6. The method according to claim 1, wherein said transformation rule includes a rotation rule and/or a translation rule and/or a warp rule, which is carried out on at least part of the section.

7. The method according to claim 1, wherein the first image field is identified at random and the subsequent image fields are identified using a pre-defined function.

8. The method according to claim 1, wherein said image field of section A is selected in the specimen by a human operator.

9. The method according to claim 1, wherein counting events are presented to a human operator as suggested counting events based on image analysis of the image field pairs.

10. A method for assessing at least two adjacent sections of a specimen, said method comprising the steps of:
 i) providing at least one corresponding image pair according to the method of claim 9; and
 ii) identifying the counting events for at least one type of object on said image fields within at least one corresponding image pair, optionally using automatic means.

11. The method according to claim 10, comprising the additional step of:
 quantifying the amount or number of said counting events on the images of said image field(s) within section A and said image field(s) within section B.

12. The method according to claim 11, wherein said quantification includes calculating the number of counting events and/or objects per volume of tissue.

13. An automated system for carrying out the method according to claim 1, comprising, in combination:
 a database capable of including a plurality of digital images of a plurality of biological specimens;
 a software module for analyzing a plurality of pixels from a digital image of a biological specimen;
 a control module comprising instructions for carrying out the method of claim 1.

14. The automated system according to claim 13, wherein said system comprises a slide loader, a barcode reader, a microscope and a stage.

15. A software program comprising instructions for carrying out the method according to claim 1.

16. The method according to claim 1, wherein the superimages are obtained from physical or virtual microscope slides.

17. The method according to claim 1, wherein at least steps c)-e) are carried out on a computer.

* * * * *